United States Patent
Abbas

(10) Patent No.: US 11,315,692 B1
(45) Date of Patent: Apr. 26, 2022

(54) SYSTEMS AND METHODS FOR VIDEO-BASED USER-INTERACTION AND INFORMATION-ACQUISITION

(71) Applicant: VitalChat, Inc., Ashburn, VA (US)

(72) Inventor: Ghafran Abbas, Ashburn, VA (US)

(73) Assignee: VitalChat, Inc., Ashburn, VA (US)

( * ) Notice: Subject to any disclaimer, the term of this patent is extended or adjusted under 35 U.S.C. 154(b) by 0 days.

(21) Appl. No.: 16/269,367

(22) Filed: Feb. 6, 2019

(51) Int. Cl.
*G16H 80/00* (2018.01)
*G16H 10/20* (2018.01)
(Continued)

(52) U.S. Cl.
CPC ............. *G16H 80/00* (2018.01); *G06F 3/017* (2013.01); *G06K 9/00335* (2013.01); *G06K 9/00711* (2013.01); *G06N 3/08* (2013.01); *G16H 10/20* (2018.01); *H04L 65/40* (2013.01); *G06K 2209/01* (2013.01)

(58) Field of Classification Search
CPC ........ A61B 5/0022; A61B 2017/00207; A61B 5/1118; A61B 5/486; A61B 5/7275; G06F 3/011; G06F 3/016; G06F 3/017; G06F 19/3418; G06F 2203/011; G06Q 50/24; G06Q 10/10; G16H 10/60; G16H 50/20;
(Continued)

(56) References Cited

U.S. PATENT DOCUMENTS 6,964,023 B2 * 11/2005 Maes .................. G06K 9/00248 715/811
9,195,968 B2 11/2015 Caldwell et al.
(Continued)

FOREIGN PATENT DOCUMENTS

WO  WO-2005084209 A2 *  9/2005  ............. G09B 23/28
WO  WO 2018/083679   5/2018
WO  WO 2018/112445   6/2018

OTHER PUBLICATIONS

Sung-Kwan Kang, Kyungyong Chung and Jung-Hyun Lee. Real-Time Tracking and Recognition Systems for Interactive Telemedicine Health Services. Springer Science+Business Media. New York: Published online: Jun. 19, 2014 (Year: 2014).*
(Continued)

*Primary Examiner* — Linh Giang Le
(74) *Attorney, Agent, or Firm* — Cooley LLP

(57) ABSTRACT

Devices, systems, and methods for real-time video processing and video-based user-interfacing via a videobot are provided. In an aspect, a first compute device receives a videobot deployment request with respect to a communication session with a user at a second compute device. A videobot is provisioned in response to the videobot deployment request to provide a real-time, video-based user-interface between the user and the videobot via the second compute device. A multimedia stream associated with the videobot is sent to the second compute device to cause the second compute device to render the videobot during the communication session. A live multimedia stream associated with the user is received from the second compute device. A user gesture event indicative of patient intake information is detected in connection with an act by the user during the communication session based on at least one video frame of the live multimedia stream.

23 Claims, 7 Drawing Sheets

(51) Int. Cl.
  *G06N 3/08* (2006.01)
  *G06F 3/01* (2006.01)
  *G06K 9/00* (2022.01)
  *H04L 65/40* (2022.01)
(58) Field of Classification Search
  CPC ........... A61N 1/36132; H04N 5/23219; G06K 9/00302
  USPC .......................................................... 705/2
  See application file for complete search history.

(56) References Cited

U.S. PATENT DOCUMENTS

| | | | |
|---|---|---|---|
| 2007/0273504 A1* | 11/2007 | Tran | A61B 5/0022 340/539.12 |
| 2011/0261213 A1* | 10/2011 | Rottler | G06F 3/04883 348/211.6 |
| 2013/0232430 A1 | 9/2013 | Reitan | |
| 2015/0347399 A1 | 12/2015 | Aue et al. | |
| 2017/0250936 A1 | 8/2017 | Rosenberg et al. | |
| 2017/0366478 A1 | 12/2017 | Mohammed et al. | |
| 2018/0001184 A1* | 1/2018 | Tran | H04N 5/2257 |
| 2018/0131808 A1* | 5/2018 | Klein | H04M 3/5191 |
| 2018/0150739 A1 | 5/2018 | Wu | |

OTHER PUBLICATIONS

"Omni_Bot_2018" reference titled "SmartAction Introduces Omnibot™, the First Omnichannel Customer Self-Service," PR Newswire, May 1, 2018, 2 pages, https://dialog.proquest.com/professional/docview/2032688006/fulltext/166132FFC51313AABB4/8?accountid=157282.

"Top 5 Chatbot Platforms to Develop Bots—Make a Choice," Feb. 28, 2018, 12 pages, https://www.newgenapps.com/blog/top-5-chatbot-platforms-develop-bots-sdk-solution-tools.

"IV.AI; The AI Agency IV.AI Launches Artificial Intelligence Backed Interactive Site for Popular," PR Newswire, Mar. 9, 2017, 2 pages, https://dialog.proquest.com/professional/docview/187787844/fulltext/16612EC5BCF88C7520/12?accountid=157282.

* cited by examiner

SYSTEMS AND METHODS FOR VIDEO-BASED USER-INTERACTION AND INFORMATION-ACQUISITION

TECHNICAL FIELD

The present disclosure relates generally to video processing, and in particular, to real-time video processing and video-based user-interfacing via an autonomous software agent, or bot.

BACKGROUND

Bots, or autonomous software agents such as videobots, chatbots, talkbots, artificial conversational or interactive entities, and the like ("bot(s)"), are software programs that may be configured to perform and automate various tasks including tasks over a network (e.g. the Internet). For example, a bot may be configured to operate as part of a user interface such as a human-machine or -computer interface (respectively, "HMI" or "HCI") to enable and facilitate interaction and communication with a user.

In some instances, for example, a bot may be configured to operate in a communication system to (a) interact with a user in a communication session, and (b) detect, associate, classify, acquire, and/or generate data and information associated with the user based on interactions between the bot and the user during the communication session. The bot may be configured to operate in a communication system to interact with a user during a communication session—to detect, determine, and enable action by the performance of tasks in response to user requests, based on one or more interactions during the communication session.

SUMMARY

According to various aspects of the present disclosure, a non-transitory processor-readable medium storing code representing instructions for execution by a processor is provided. In an aspect, the instructions may be executed by the processor to receive, from a first compute device, a videobot deployment request with respect to a communication session with a user at a second compute device. The instructions may be executed by the processor to provision a videobot instance to provide a real-time, video-based user-interface between the user and the videobot instance via the second compute device in response to the videobot deployment request. The instructions may be executed by the processor to send, to the second compute device, a multimedia stream associated with the videobot instance to cause the second compute device to render the videobot instance during a time period of the communication session. The instructions may be executed by the processor to receive, from the second compute device during the time period, a live multimedia stream associated with the user and received during the time period. The instructions may be executed by the processor to detect a user gesture event in connection with an act by the user during the time period based on at least one video frame of the live multimedia stream received during the time period, the user gesture event corresponding to an indication of a set of patient intake information associated with the user. In response to detecting the user gesture event, the instructions may be executed by the processor to send, to the first compute device, a signal indicating the user gesture event.

According to various aspects of the present disclosure, a non-transitory processor-readable medium storing code representing instructions for execution by a processor is provided. In an aspect, the instructions may be executed by the processor to generate a videobot deployment request with respect to a communication session. The instructions may be executed by the processor to send, to a first compute device, the videobot deployment request. The instructions may be executed by the processor to receive, from a second compute device in response to sending the videobot deployment request, a multimedia stream associated with a videobot instance. The instructions may be executed by the processor to render the videobot instance based on the multimedia stream during a first time period of the communication session to provide a real-time, video-based user-interface between a user and the videobot instance. The instructions may be executed by the processor to send, to the second compute device during the first time period, a live multimedia stream associated with the user. The instructions may be executed by the processor to determine a first frame process window ("FPW") value based on a frame rate of rendering of the videobot instance during the first time period. The instructions may be executed by the processor, in response to determining that the first FPW value exceeds a predetermined threshold, to perform a remedial action to define a frame rate of rendering the videobot instance during a second time period of the communication session after the first time period, a second FPW value of the videobot instance during the second time period being based on the frame rate of the rendering the videobot instance during the second time period and being less than the first FPW value.

According to various aspects of the present disclosure, a non-transitory processor-readable medium storing code representing instructions for execution by a processor is provided. In an aspect, the instructions may be executed by the processor to generate a videobot deployment request with respect to a communication session with a user at a first compute device, to provide a real-time, video-based user-interface between the user and the first compute device via a videobot instance. The instructions may be executed by the processor to send, to the second compute device, the videobot deployment request to cause the first compute device to render the videobot instance during the communication session based on a multimedia stream associated with the videobot instance. The instructions may be executed by the processor to receive, from the second compute device, a signal indicating a user gesture event in connection with an act by the user during the communication session. The instructions may be executed by the processor to generate a videobot command including a patient intake query based on the user gesture event. The instructions may be executed by the processor to send, to the second compute device, the videobot command to cause the first compute device to render the videobot instance in conjunction with the patient intake query. The instructions may be executed by the processor to receive, from the second compute device, a response by the user to the patient intake query, the response including an indication of patient intake information associated with the user.

DETAILED DESCRIPTION

Figure 1:
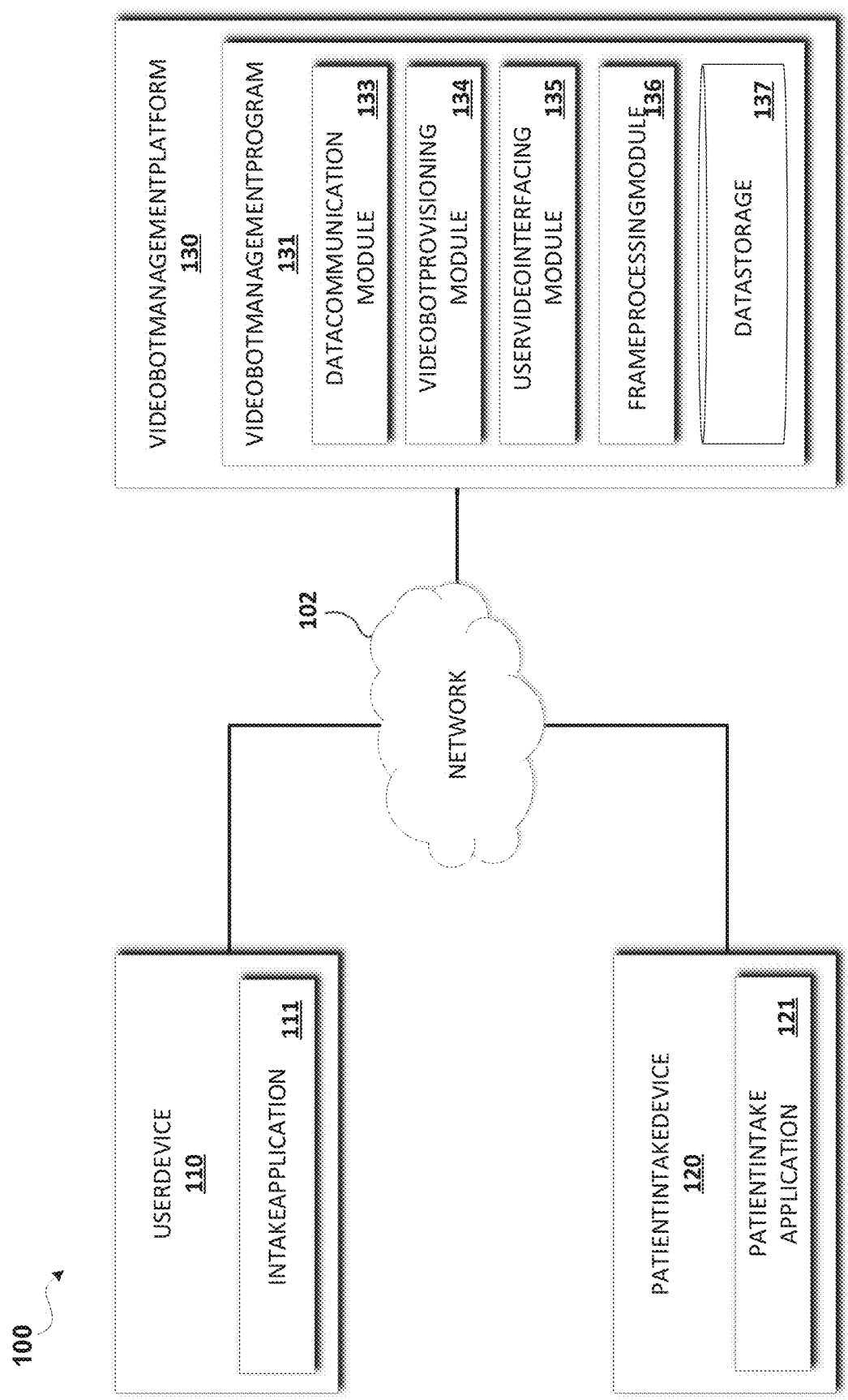
FIG. 1 is a functional block diagram depicting a videobot management system, in accordance with an embodiment of the present disclosure.

An interaction, event, or user gesture event ("interaction event(s)" or "user gesture event(s)") between a bot and a user—such as in or during a communication session hosted over a network—may occur via one or more modes of communication, including, for example, verbal communication, nonverbal communication, and the like. Verbal communications may include, for example, verbal, written, or recorded messages—such as may be conveyed linguistically by written language (e.g. text, email), verbal or spoken language (e.g. audio, acoustics), or the like. Nonverbal communications may include, for example, non-verbal or non-written messages, such as may be conveyed nonlinguistically—such as in a non-written language, a nonverbal or non-spoken language, or the like (e.g. body language, bodily signals, sign language).

Nonverbal communication is the nonlinguistic transmission of information through visual, auditory, tactile, and/or kinesthetic (physical) channels. Nonverbal communications may be consciously or otherwise expressed, exhibited, or communicated—such as by visual appearance, haptics (e.g. via behaviors involving touch), characteristics of speech or voice, and/or body language including, for example, gestures, facial expressions, posture, gaze, and/or other behaviors, acts, or cues (collectively, "body language" or "gesture(s)"). Generally, nonverbal communication can be classified into three principal areas: environmental conditions where communication takes place, physical characteristics of the communicators, and behaviors of communicators during interaction. For example, nonverbal communication may include the use of visual cues such as body language (kinesics), distance (proxemics) and/or physical environments/appearance, of voice (paralanguage) and/or of touch (haptics). Nonverbal communication may also include the use of time (chronemics), eye contact and the actions of looking while talking and listening, frequency of glances, patterns of fixation, pupil dilation, and blink rate (oculesics).

Nonverbal communications may be observed or otherwise perceived by humans via various sensory modalities such as sight (vision), hearing (audition), smell (olfaction), taste (gustation), and/or touch (somatosensation). An observed nonverbal communication may be interpreted or decoded with respect to a context of an interaction such as based on body language (e.g., via kinesics or interpretation of body motion), characteristics of speech or voice (e.g., via paralanguage), use of space (e.g., via proxemics or use of space), touch or haptics, and/or chronemics (the role and effect of time on communication).

Nonverbal communication can contribute significantly to the meaning of a message to various degrees. For example, the context of an interaction event can influence, affect, and change the meaning of an instance of nonverbal communication to various degrees. Moreover, conflicting verbal and nonverbal communications (e.g., messages) within the same interaction event can sometimes convey opposing or conflicting messages, or otherwise lead to miscommunication. For example, in communicating a message in an interaction, a person verbally expressing a statement of truth via verbal communication while simultaneously fidgeting or avoiding eye contact via nonverbal communication may convey a mixed message to the receiver in the interaction that is indicative of deceit. The communicated message, if conveyed without the portion related to the nonverbal communication, may result in such deceit going unnoticed or undetected.

This can be problematic for certain types of automated communication systems in which interactions between bots and users—such as in a communication session hosted over a network—are limited to interactions on the basis of communicated messages that include only or mostly verbal communication (e.g., via verbal, written, or recorded messages, such as in a chatroom) due to various technical limitations, which commonly results in miscommunication. For example, during a communication session such as a text-, audio-, and/or video-based call, audio and/or video signals can, to an extent, be transmitted between nodes of the network, thereby allowing users to transmit and receive audio data (such as speech) and/or video data (such as streaming video) to each other in the communication session hosted over the network. In some cases, however, only the audio signals may be transmitted between the nodes of the network due to, for example, limitations of the network or the communication system, which may result in limited bandwidth.

The performance and effectiveness of bots configured to enable and facilitate interactions and communications with users, such as for the purpose of automating a task, depends on the degree to which the bots may effectively and efficiently observe, perceive, and interpret nonverbal communications—in conjunction with verbal communications or otherwise—to accurately interpret, understand, and respond to user input. For example, where attempts by users to interact or otherwise communicate are limited to verbal or linguistic modes of communication, such bots may perform sufficiently by perceiving text- or audio-based communication for response to user input; some attempts to communicate, however, may also or otherwise include nonverbal modes of communication, such as may be expressed by body language, and the like, which may not be communicated due to various technical deficiencies.

Accordingly, a need exists for devices, systems, and methods that overcome the aforementioned problems and deficiencies. Embodiments of the present disclosure are directed to devices, systems, and methods of real-time video processing and video-based user-interfacing via an autonomous software agent, or bot. Advantageously, such embodiments may be implemented to enable bots to interact and communicate with users—verbally, non-verbally, and/or otherwise—such as in a communication session hosted over a network.

FIG. 1 is a functional block diagram depicting videobot management system 100, in accordance with an embodiment. As shown, videobot management system 100 may include user device 110, patient intake device 120, and videobot management platform 130 interconnected over network 102. While videobot management system 100 is depicted in FIG. 1 as including three discrete devices, other arrangements may be contemplated. For example, the videobot management platform 130 may instead be suitably formed of one or more integrated devices.

In some implementations, network 102 may include, for example, an intranet, a local area network (LAN), a personal area network (PAN), a wireless local area network (WLAN), a wireless personal area network (WPAN), and/or a wide area network (WAN) such as the Internet, and may include wired, wireless, and/or fiber optic connections. Network 102 may otherwise be or include any combination of connections and protocols configured to support communications between user device 110, patient intake device 120, and/or videobot management platform 130, in accordance with embodiments of the present disclosure.

In some implementations, user device 110, patient intake device 120, and/or videobot management platform 130 may individually be or include, for example, a computing platform or node such as a wearable device, an implantable device, a mobile or smart phone, a tablet computer, a laptop computer, a desktop computer, a server such as a database server, a virtual machine, and the like. User device 110, patient intake device 120, and/or videobot management platform 130 may otherwise be or include any other suitable type of computing platform, computer system, information system, or information content processing device capable of enabling communications between devices, such as one or more of user device 110, patient intake device 120, and/or videobot management platform 130 via a network such as network 102, in accordance with embodiments of the present disclosure. In some implementations, user device 110, patient intake device 120, and/or videobot management platform 130 may include internal and external hardware components, such as described with reference to FIG. 5. In other implementations, user device 110, patient intake device 120, and/or videobot management platform 130 may be implemented via a cloud computing environment such as described with reference to FIGS. 6-7.

User device 110 hosts intake application 111. User device 110 may implement a combination of devices and technologies such as network devices and device drivers to support the operation of intake application 111 and provide a platform enabling communications (e.g., via network 102) between user device 110, patient intake device 120, and/or videobot management platform 130, in accordance with embodiments of the present disclosure. Data sent and received by user device 110 may be stored on one or more computer readable storage media for retrieval and use by intake application 11, as described in further detail herein. In some implementations, user device 110 may include an image capture device such as a camera, webcam, or the like.

Intake application 111 may be or include an application or program such as a software program, one or more subroutines contained in a program, an application programming interface, or the like. Intake application 111 communicates (e.g., sends, receives) data with respect to one or more applications or programs hosted or resident on one or more other compute devices, such as patient intake device 120 and/or videobot management platform 130, as described in further detail herein. In some implementations, data sent and received by user device 110 (e.g., via intake application 111) may include, for example, one or more data streams such as a multimedia stream or a live stream. For example, during a communication session in which user device 110 is connected or otherwise in communication (e.g., via intake application 111) with one or more other compute devices (e.g., videobot management platform 130), the data sent and received by user device 110 may include a multimedia stream associated with a videobot instance, with which a user of user device 110 may interact, as described in further detail herein. For example, in some implementations, intake application 111 may be or include one or more applications configured to communicate with videobot management platform 130 via a software development kit (SDK) or application programming interface (API), such as to run commands and webhooks for event subscription, and the like.

Patient intake device 120 hosts patient intake application 121. Patient intake device 120 may implement a combination of devices and technologies such as network devices and device drivers to support the operation of patient intake application 121 and provide a platform enabling communications (e.g. via network 102) between user device 110, patient intake device 120, and/or videobot management platform 130, in accordance with embodiments of the present disclosure. Data sent and received by patient intake device 120 may be stored on one or more computer readable storage media for retrieval and use by patient intake application 121, as described in further detail herein.

Patient intake application 121 may be or include an application or program such as a software program, one or more subroutines contained in a program, an application programming interface, or the like. Patient intake application 121 communicates (e.g. sends, receives) data with respect to one or more applications or programs hosted or resident on one or more other compute devices, such as user device 110 and/or videobot management platform 130, as described in further detail herein.

In some implementations, the data sent and received by patient intake device 120 (e.g., via patient intake application 121) may include, for example, data signals corresponding to executable videobot commands or instructions, as described in further detail herein. For example, during a communication session in which compute devices such as user device 110 and videobot management platform 130 are connected or otherwise in communication, the data sent and received by patient intake device 120 may include data signals representing or indicating executable videobot commands configured to be executed to control a videobot instance with which a user of user device 110 may interact, as described in further detail herein. For example, the commands may be executed to play video, play audio, show image, show webpage, and/or the like.

Videobot management platform 130 hosts videobot management program 131. Videobot management platform 130 may implement a combination of devices and technologies such as network devices and device drivers to support the operation of videobot management program 131 and provide a platform enabling communications (e.g., via network 102) between user device 110, patient intake device 120, and/or videobot management platform 130, in accordance with embodiments of the present disclosure. Data sent and received by videobot management platform 130 may be stored on one or more computer readable storage media for retrieval and use by videobot management program 131, as described in further detail herein.

Videobot management program 131 includes data communication module 133, videobot provisioning module 134, user video interfacing module 135, frame processing module 136, and data storage 137. Videobot management program 131 may be an application or program such as a software program, one or more subroutines contained in a program, an application programming interface, or the like. In some implementations, videobot management program 131 may be configured to implement one or more natural language processing algorithms, pattern matching or recognition algorithms and/or neural networks to enable, establish, facilitate, and/or provide real-time video processing and video-based user-interfacing via a videobot, as described herein.

Data communication module 133 communicates with compute devices (e.g., user device 110, patient intake device 120) with respect to a communication session to send and receive videobot data to enable and facilitate interactions and communications between a user (e.g., of user device 110) and a video bot instance. Data communication module 133 stores the videobot data in data storage 137 for retrieval and use by videobot management program 131 before and during a communication session, as described herein. In some implementations, the videobot data sent by data communication module 133 may include a multimedia stream associated with a videobot instance, configured to cause the second compute device to render the videobot instance during a time period of the communication session for interaction with a user (e.g., of user device 110), as described herein. For example, in some implementations, the videobot data may include instructions, commands, or code such as digital image instructions, digital visualization rendering instructions, and/or the like. The videobot data may alternatively or additionally include any other suitable type of instruction, command, or code configured to cause the second compute device to render the videobot instance during the communication session, in accordance with embodiments of the present disclosure. In such implementations, the videobot data received by data communication module 133 may alternatively or additionally include one or more data signals representing or indicating a videobot deployment request corresponding to a request to deploy the videobot instance to the communication session for interaction with the user at user device 110 during the communication session.

Videobot provisioning module 134 provisions a videobot instance to provide a real-time, video-based user-interface between the user and the videobot instance via user device 110 in response to a received videobot deployment request. In some implementations, videobot provisioning module 134 generates instructions representing or indicating the multimedia stream based on the videobot deployment request. Moreover, the instructions may be executed to deploy or send, to the second compute device, the multimedia stream associated with the videobot instance to cause the second compute device to render the videobot instance during a time period of the communication session. Moreover, the instructions may be executed to receive, from the second compute device during the time period, a live multimedia stream associated with the user and received during the time period.

User video interfacing module 135 receives, from user device 110 during the time period, a live multimedia stream associated with the user. In some implementations, user video interfacing module 135 generates instructions for execution to detect a user gesture event in connection with an act by the user during the time period based on at least one video frame of the live multimedia stream received during the time period. In some instances, the user gesture event includes a symptomatic act by the user during the communication session. The symptomatic act may include, for example, an act or behavior exhibited by the user that is indicative of a symptom or sign of a condition such as a medical condition. For example, in some instances, the user gesture event may include verbal communication, nonverbal communication, and the like. In some instances, the real-time, video-based user-interface is configured to collect medical data associated with the user based on the live multimedia stream associated with the user. In some instances, the user gesture event may correspond to an indication of a set of patient intake information associated with the user. For example, in some instances, the patient intake information may include a medical history of the user.

In some implementations, user video interfacing module 135 may generate the instructions for execution in real-time to detect a user gesture event based on audio and/or video of the user at user device 110 during the communication session. In some implementations, user video interfacing module 135 may implement one or more natural language processing algorithms, pattern matching or recognition algorithms, and a neural network to enable, establish, facilitate, and provide real-time video processing and video-based user-interfacing via a videobot. In such implementations, the natural language processing algorithms and the pattern matching or recognition algorithms may include, for example, algorithms configured for head gesture detection, hand gesture detection, medical device OCR detection, prescription detection, and/or speech recognition.

In some implementations, the pattern recognition algorithm may include a computer vision algorithm and a speech recognition algorithm. In such implementations, the pattern recognition algorithm may additionally include a gesture detection algorithm, an optical character recognition algorithm, and/or a barcode processing algorithm. In such implementations, the neural network may include a recurrent neural network such as a long short-term memory (LSTM) recurrent neural network.

Frame processing module 136 generates instructions for execution to determine a first frame process window ("FPW") value based on a frame rate (e.g., in frames per second) of the rendering of the videobot instance by user device 110 during the first time period. An FPW value may be defined as the amount of time available to process, by one or more algorithms, a single frame (e.g., video frame) in a multimedia stream, which may be determined based on the frame rate (e.g., in frames per second) of the multimedia stream associated with the videobot instance. Frame process times ("FPT(s)"), of the one or more algorithms may be determined by measurement of the time required by each of the one or more algorithms to process the single frame. The FPT of each algorithm can vary based on hardware, network conditions, video frame quality, and the like (e.g., of user device 110, of network 102), by which each algorithm may be implemented. An actual frame process window ("AFPW") may be defined as the actual time taken to process the single frame in the multimedia stream by the one or more algorithms combined, which may be determined by summation of the FPT of each algorithm. In some implementations, the instructions may be executed to determine that the first FPW value exceeds a predetermined threshold. The predetermined threshold may correspond, for example, to the amount of time available to process each frame in the multimedia stream so as to provide, facilitate, and maintain real-time video processing, in accordance with embodiments of the present disclosure. In other words, the predetermined threshold may correspond to the amount of time made available by a particular device or system (e.g., user device 110) to process the single frame in the multimedia stream, which may depend on the limitations, capabilities, and resources of the device or system. Generally, the AFPW value for the one or more algorithms should always be less than the FPW value as may be determined based on a frame rate (e.g., in frames per second) of the rendering of the videobot instance by user device 110.

In some implementations, videobot management system 100 may be system hardware agnostic. For example, the videobot management system 100 can be configured to work with SIP devices, H.323 devices, and Webrtc devices, which include browsers, desktop, and mobile apps. The signaling between the server (e.g., videobot management platform 130) and the user's compute device (e.g., user device 110) can be managed and translated by a software module at the server. Thus, no additional software/agent need to be downloaded at the user's compute device. Video calls/sessions between each user compute device and the server can be handled, for example, peer-to-peer using the Session Description Protocol (SDP).

As an example, in some implementations, videobot management system 100 may be or include a cloud-based system that provides external applications the ability to provide interactive automated real-time video for medical purposes (e.g., patient intake, diagnosis, prognosis). For example, videobot management system 100 may include or implement a communications infrastructure compliant with SIP, H323, and Webrtc protocols to establish the communication session. Videobot management system 100 may be configured to automate collection of information associated with a user (e.g., patient, subject), such as medically relevant information associated with the user, which may be, for example, used to diagnose the user's symptoms or passed along to a medical professional for further analysis. Subsequently, the user can be, for example, forwarded to a call with a real human medical professional. Moreover, in some implementations, user video interfacing module 135 analyzes the video and audio streams of a livestream associated with a user to send event notifications to one or more external applications (e.g., patient intake device 120), which can then send commands to videobot management platform 130 for interactivity. The videobot collects medically relevant information the user via video, audio, and medical peripherals such as digital stethoscopes, digital horoscopes, blood pressure monitors, electrocardiogram ("EKG" or "ECG") monitors, heartbeat monitors, blood pressure monitors, thermometers, endoscopes, and many others. Moreover, during a video call with the videobot, intake information about the patient is collected based on event recognitions based on detected head poses, hand poses, and medical peripherals. This intake information is sent to the external applications for storage and processing in real-time. The external application is then able to send commands to the videobot to respond to the user to show images, videos, play audio, or play a human face. In such implementations, optical character recognition (OCR) and barcode (e.g., QR code) recognition technologies are used to detect reading from medical devices and sent to EA. The videobot management system 100 is able to analyze (e.g., via videobot management platform 130) the frames in the video stream to automatically recognize the medical device and read the output automatically, simply by showing results to the camera.

As another example, in some implementations, the medical peripherals data is collected via an SDK on the client (e.g., user device 110), and is then transmitted to videobot management program 131 for processing, as described herein. This data collection can be agnostic to the type of device and/or platform used. Each peripheral may have unique protocols or data transfer methods that are to be collected and send to the SDK for interoperability. For example, medical peripherals are automatically recognized during the video call when shown to the camera, then the videobot is able to OCR the readings from the device and send to an external application (e.g., patient intake application 121) automatically.

Figure 2:
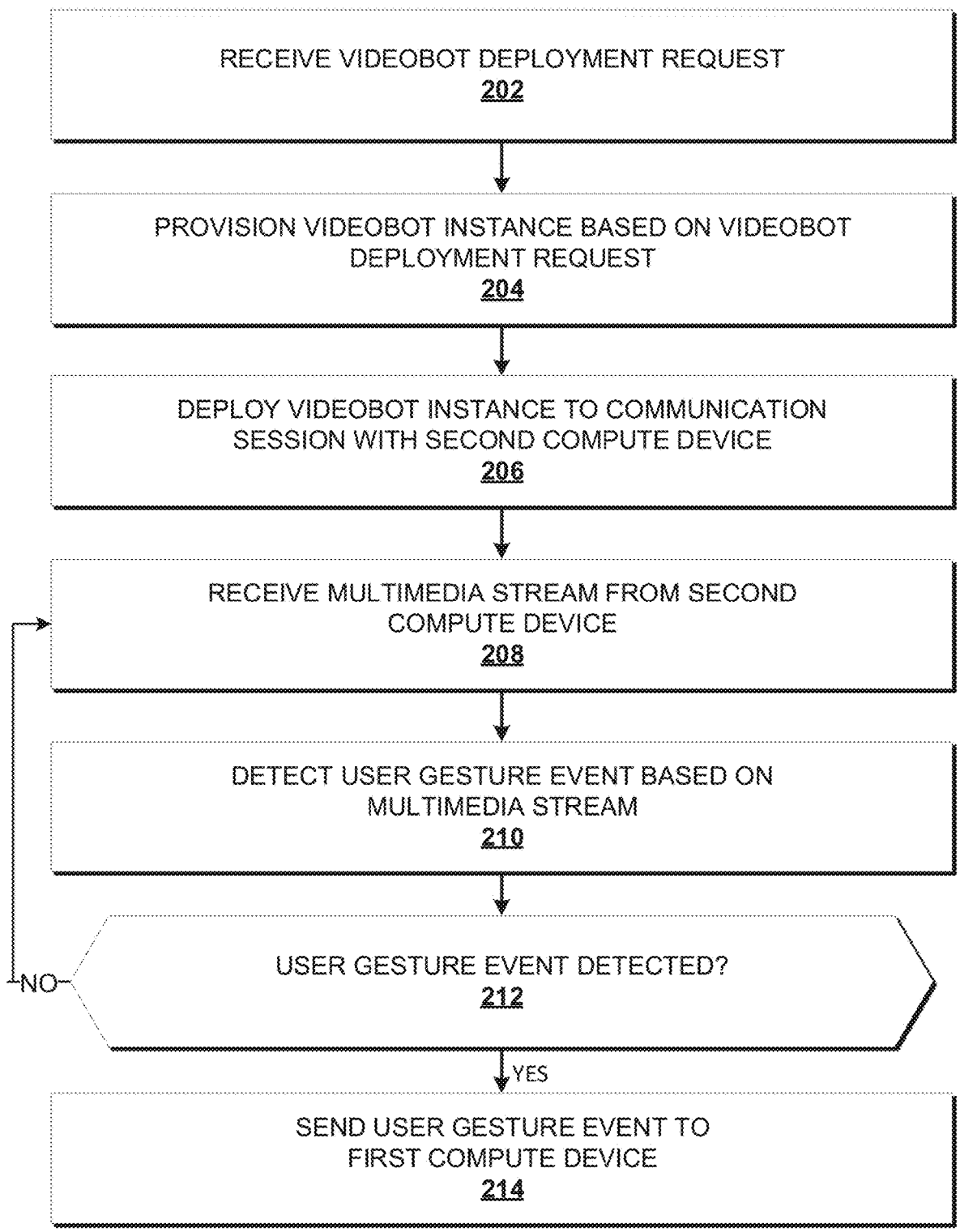
FIG. 2 is a flowchart depicting an example operation of an aspect of a videobot management system, in accordance with an embodiment.

FIG. 2 is a flowchart depicting an example operation of an aspect of videobot management system 100, in accordance with an embodiment. In some implementations, for example, the example operation may be performed via a device, platform, or the like, such as videobot management platform 130.

At 202, data communication module 133 receives, from a first compute device, a videobot deployment request with respect to a communication session with a user at a second compute device. In some implementations, the first compute device and the second compute device may include, for example, patient intake device 120 and user device 110, respectively.

At 204, videobot provisioning module 134 provisions a videobot instance to provide a real-time, video-based user-interface between a user and the videobot instance via the second compute device in response to the videobot deployment request.

At 206, data communication module 133 sends, to the second compute device, a multimedia stream associated with the videobot instance to cause the second compute device to render the videobot instance during a time period of the communication session. The multimedia stream may be sent, to cause deployment of the videobot instance, to the communication session for interaction with the user during the communication session.

For example, in some implementations, when an external application (e.g., patient intake device 120) signals videobot management program 131 to dial out (or signal) to a user, in which case the call (or session) is initiated by deployment of a videobot instance, the following workflow is performed: (a) a session is created, (b) a dial out (or signal) function (e.g., to user device 110) is performed, (c) the videobot instance is provisioned or created, (d) the videobot instance is signaled for deployment to a communication session, (e) an SDP offer for communication to user device 110 is generated and sent, to which an SDP answer (e.g., generated by user device 110) is received in response, and (f) a video call (e.g., communication session) is started with the user at user device 110. As another example, when patient intake device 120 signals videobot management platform 130 to answer a call from a user, in which case the call (or session) is initiated by the user's device, the workflow may include: user device 110 generates and sends an SDP offer to videobot management platform 130, videobot management platform 130 notifies patient intake device 120 in response to the SDP offer, patient intake device 120 establishes a communication session, executes a dial-in function, creates a videobot, commands the videobot to generate and send an SDP answer to user device 110 via patient intake device 120, and then a video call (e.g., communication session) is started with the user at user device 110

At 208, data communication module 133 receives, from the second compute device during the time period, a live multimedia stream associated with the user and received during the time period.

At 210, user video interfacing module 135 detects an interaction or user gesture event in connection with an act by the user during the time period based on at least one video frame of the live multimedia stream received during the time period. In some implementations, the user gesture event may correspond to an indication of a set of patient intake information associated with the user. For example, in some implementations, user video interfacing module 135 may be configured to monitor, on a frame-by-frame basis, the communication session via a videobot instance based on video and/or audio (e.g., corresponding to verbal communications and/or nonverbal communications) associated with a user at a user device (e.g., user device 110) in the communication session to detect interaction or gesture events for communication to patient intake device 120 and response (e.g., via query) to the events via videobot instruction generated by patient intake device 120.

At 212, if the user gesture event has not been detected, the live multimedia stream associated with the user continues to be received, such as at 208. If, at 212, the user gesture event has been detected, then at 214, in response to detecting the user gesture event, data communication module 133 sends, to the first compute device, a signal indicating the user gesture event.

In some implementations, for example, a head or hand pose gesture recognition algorithm may be implemented, for each video frame of a multimedia stream associated with a videobot, to detect locations of key body points (e.g., of a facial region, of an upper torso region, of a hand(s) region) with respect to the user. Input data representing (or indicating) the key body points may be input to a neural network such as a recurrent neural network or an LSTM recurrent neural network (e.g., for gesture classification), to detect time-series driven deviations or abnormalities in the gestures and/or behaviors of the user, and to communicate a detected event (e.g. to patient intake device 120).

In some implementations, for example, a medical device or prescription recognition algorithm may be implemented, for each video frame of a multimedia stream associated with a videobot, to detect interaction events relating to medicinal or health-related peripherals such as medical devices, medical containers, and the like. In such implementations, the medical device or prescription recognition algorithm may perform OCR or bar code reading with respect to the output of a medical device or medicine label on a prescription container to detect the events.

In some implementations, the time period is a first time period and the set of patient intake information is a first set of patient intake information. In such implementations, in response to sending the signal indicating the user gesture event, a signal indicating a videobot command may be received from patient intake device 120. In such implementations, the videobot command may be executed to cause the second compute device to render the videobot instance (e.g., at user device 110) in conjunction with a patient intake query during a second time period of the communication session after the first time period. In such implementations, a live multimedia stream associated with the user may be received from patient intake device during the second time period. A response to the patient intake query during the second time period may be detected based on at least one video frame of the live multimedia stream during the second time period, where the response may include an indication of a second set of patient intake information associated with the user. In response to detecting the response to the patient intake query, patient intake device may send, to the first compute device (e.g., videobot platform 130), a signal indicating the response. In such implementations, the user gesture event or the response is detected by execution of a pattern recognition algorithm in conjunction with a neural network.

Figure 3:
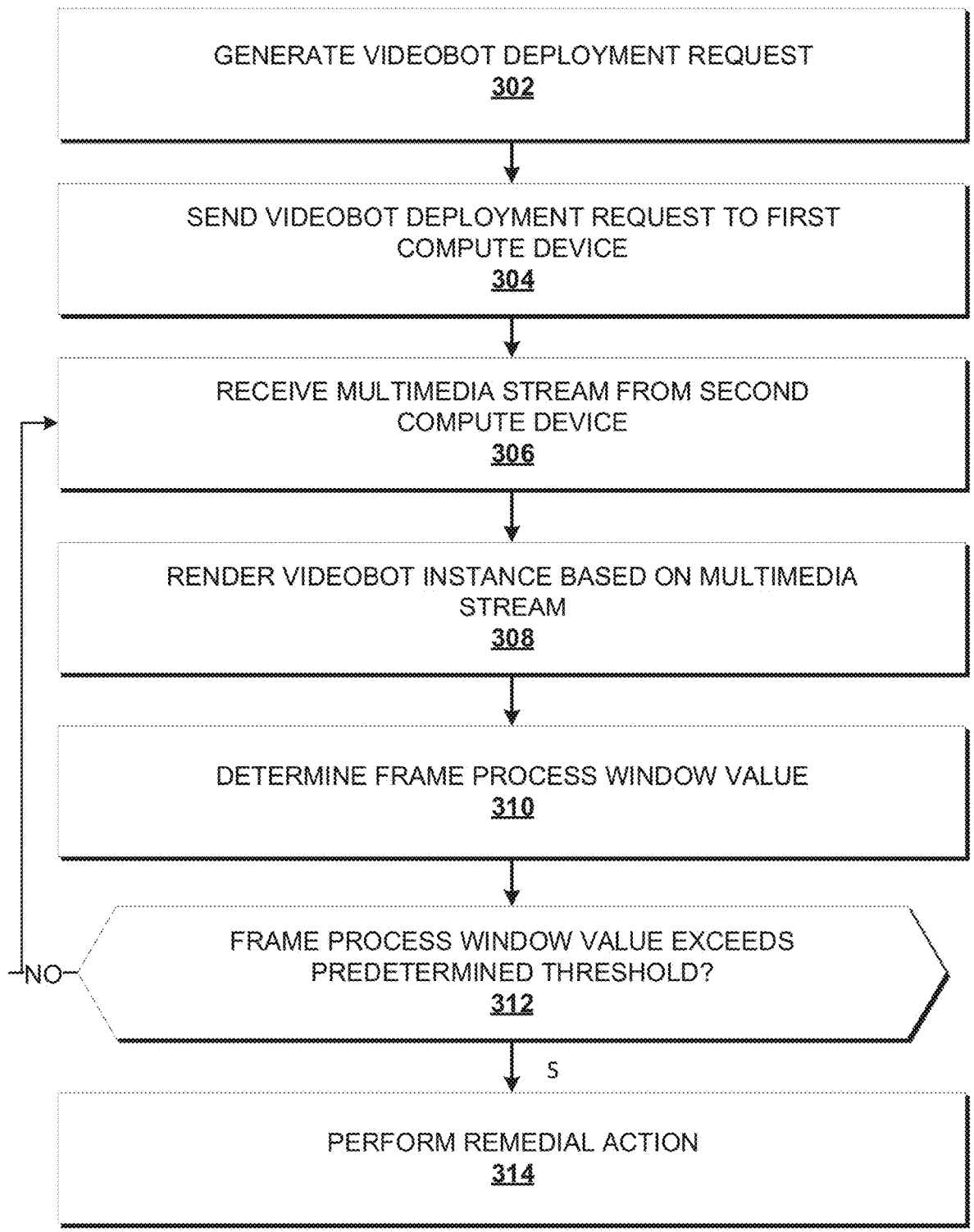
FIG. 3 is a flowchart depicting an example operation of an aspect of a videobot management system, in accordance with an embodiment.

FIG. 3 is a flowchart depicting an example operation of an aspect of videobot management system 100, in accordance with an embodiment. In some implementations, for example, the example operation may be performed via a device such as user device 110.

At 302, user device 110 generates a videobot deployment request with respect to a communication session. At 304, user device 110 sends, to a first compute device, the videobot deployment request. In some implementations, the first compute device may include, for example, patient intake device 120. At 306, user device 110 receives, from a second compute device in response to sending the videobot deployment request, a multimedia stream associated with a videobot instance. In some implementations, the first compute device may include, for example, videobot management platform 130. At 308, user device 110 renders the videobot instance based on the multimedia stream during a first time period of the communication session to provide a real-time, video-based user-interface between the user and the videobot instance.

At 310, user device 110 determines a frame process window ("FPW") value based on a frame rate of rendering of the videobot instance during a time period of the communication session according to instructions associated with a videobot command from videobot management platform 130. In some implementations, user device 110 determines a first FPW value based on a frame rate of rendering of the videobot instance during a first time period, for comparison with a second FPW of rendering of the videobot instance during a second time period.

In such implementations, user device 110 additionally determines a frame processing time ("FPT") corresponding to a processing time per frame by each actively-implemented interaction or gesture detection algorithm in the communication session, such as those implemented by user video interfacing module 135. That is, each algorithm is implemented to detect specific events in the each video frame (e.g., of a multimedia stream associated with the videobot instance). The amount of time taken by these algorithms is, on a per-frame basis, considered to be their respective FPT value or measurement. The total number of events being detected with their FPT times should be less than the FPW that is available for the stream. During a live video call, it is possible that the FPT of these algorithms are causing the actual frame process windows ("AFPW") to exceed the FPW, which can cause unpredictable/unreliable results for event detection. This can also cause major performance concerns because the high AFPW can cause a backup of frames that need to be processed with no time to catch up.

At 312, in response to determining that the first FPW value exceeds a predetermined threshold, then at 314, user device 110 performs a remedial action to define a frame rate of rendering the videobot instance during a second time period of the communication session after the first time period, such that a second FPW value of the videobot instance during the second time period, being based on the frame rate of the rendering the videobot instance during the second time period, is less than the first FPW value. At 312, if the first FPW value does not exceed the predetermined threshold, then user device 110 continues to receive, from the second compute device, the multimedia stream associated with the videobot instance, such as described with reference to 306. In some implementations, the remedial action is performed according to one or more commands received from a compute device such as videobot management platform 130. In some implementations, the predetermined threshold may be defined based on the first FPW value to thereby limit or maintain a magnitude of the first FPW value below that of the second FPW.

In some implementations, the remedial action is performed to reduce a latency between the rendering of the videobot instance and the received multimedia stream during the second time period. In some implementations, the remedial action is performed to skip at least one frame during the rendering of the videobot instance during the second time period. For example, one or more orphan frames of the multimedia stream during the second time period may be skipped based on the delta between FPW and AFPW for event processing. For example, the remedial action can be performed to reduce the latency by reducing a video frame pixel density during the second time period below that of the first time period to help reduce the FPT for all algorithms.

In some implementations, the remedial action is performed to reduce a video frame pixel density of at least one frame during the rendering of the videobot instance during the second time period, to thereby reduce a video frame pixel density and thereby reduce the FPT of all algorithms during the second time period. For example, low priority algorithms may include non-required video processing processes, like certain gesture detections or object detections, which will not impact the quality of the call if they are disabled. For example, number recognition from a user's hands/fingers can be disabled if that is not used often.

In some implementations, for every configuration of a videobot, the algorithms may be prioritized or ranked on the basis of individual algorithm performance and utility. For example, in some implementations, low priority algorithms may be identified on the basis of frequency of use, commonality number of known applicable use cases, or the like. As another example, for configurations of a videobot, the priorities of the algorithms can be customized to determine the LPVAs. The table below illustrates how the use case of the videobot and the expected gestures for the call, in turn, determines the priority. For example, various gesture detections algorithms may be prioritized such as in Table 1, below, which includes a non-limiting list of example algorithms. As an example, for any algorithms that are expected for the video call, they are not considered to be LPVAs; however, they are ranked based on commonality and expectation levels. In some implementations, commonality of an algorithm is based on previous usage of the videobot for certain use cases and how often a particular algorithm was actually detected.

TABLE 1

| Type | Algorithm | Expectation Level | Is Common for Use Case | Priority | Is LPVA |
| --- | --- | --- | --- | --- | --- |
| Face | Age Detection | High | Yes | 1 | No |
| Face | Gender Detection | High | Yes | 2 | No |
| Face | Recognize Identity | High | Yes | 3 | No |
| Facial | Neutral, Sad, Happy, etc.... | High | Yes | 4 | No |
| Head | Nod No | High | Yes | 5 | No |
| Head | Nod Yes | High | Yes | 6 | No |
| Head | Tilt | High | Yes | 7 | No |
| Head | Attention - Facing Towards Camera | High | Yes | 8 | No |
| Head | Facing Up, Down, Left Right | High | Yes | 9 | No |
| Hands | Pointing up, left, down, right | High | Yes | 10 | No |
| Hands | Thumbs Up | High | Yes | 11 | No |
| Hands | Thumbs Down | High | Yes | 12 | No |
| Hands | Thumbs Neutral | High | Yes | 13 | No |
| Hands | Wave | High | Yes | 14 | No |
| Hands | Numbers 1-10 Palm Facing | Medium | No | 15 | Yes |
| Hands | Camera Fist | Medium | No | 16 | Yes |
| Hands | Maybe Wave | Medium | No | 17 | Yes |
| Hands | OK | Medium | No | 18 | Yes |

TABLE 1-continued

| Type | Algorithm | Expectation Level | Is Common for Use Case | Priority | Is LPVA |
| --- | --- | --- | --- | --- | --- |
| Shoulders | Shrug | Low | No | 19 | Yes |
| Eyes | Towards straight, left, right, up, down | Low | No | 20 | Yes |
| Hands | Over mouth | Low | No | 21 | Yes |
| Hands | Covering eyes | Low | No | 22 | Yes |
| Hands | On head | Low | No | 23 | Yes |

In some implementations, the remedial action is performed to skip execution of at least one image processing algorithm during the second time period based on a use value of the image processing algorithm relative to a use value of at least one other image processing algorithm. For example, the use value may be used as a measure of relative utility or performance of each of the algorithms, such as with respect to detecting a particular interaction or gesture event. In other words, skipping execution of at least one image processing algorithm based on utility can reduce the AFPW time of each algorithm. Accordingly, the AFPW may be maintained under the FPW with respect to processing by a particular algorithm by disabling certain algorithms from processing. We determine the priority of each algorithm based on certain factors, then enable/disable algorithms as needed during the video call, until the AFPW is below the FPW. In some implementations, the remedial action is performed to execute at least two image processing algorithms in parallel during the second time period. This can help to reduce the AFPW by running the algorithms in separate CPUs to reduce total processing time.

In some implementations, the remedial action is performed in response to determining that an actual FPW is greater than a determined FPW. For example, if there are no more LPVAs to disable, then processing frames can be skipped based on the AFPW value. This will reduce the quality of the algorithms but will keep the processing of the video in real-time. As another example, if there are no more LPVAs to disable, parallel processing threads can be activated to run the algorithms at the same time to reduce the AFPW. This option is available for videobots configured to run on more expensive hardware that have high performance CPU and GPU processors.

For purposes of the present disclosure, real-time video processing is defined as the ability to perform recognitions and processes of the system one frame at a time as frames are received in the video stream. For example, before the next frame arrives in the video stream, all the algorithms are to have already completed. Advantageously, this overcomes various of the aforementioned known problems, as buffering or re-sampling currently cannot be used in instant machine vision tasks to provide instant feedback to the user. This is due to this tendency that known algorithms and image processing libraries cannot be used. All processing by each detection algorithm are to be done frame-by-frame as they come. For example, the FPW may be determined with respect to a multimedia stream associated with the videobot instance, in which the window of processing frames in real-time is determined by the frame rate at which the video is streaming. For a normal video call, the frame rate can be 30 fps or 60 fps. If the FPS is 30, the FPW is approximately 33 milliseconds, corresponding to approximately 33 milliseconds to perform the event recognitions for a single frame in the video stream.

For example, during a real-time communication session, video streams perform adaptive techniques to respond to network issues such as changing video quality and reducing frame rates. Because of this, the number of frames being received per second to the videobot constantly changes during the call, which can be responded to to maintain real-time video processing, in accordance with embodiments of the present disclosure. That is, if the frames are fewer, more time exists to process each frame. Also, if the frame rate increase, less time exists to process each frame.

In some implementations, non-interval based real-time processing may be implemented such that the interaction or gesture detection algorithms are run using a custom time series-based algorithm. For example, using machine-vision, landmarks for the head and hands are detected, which are then fed to a time-series-based pre-trained neural network to detect gestures. These gestures include, for example, head nodding, finger pointing, hand waving, thumbs-up, thumbs-down, and many more gestures. Thus, frame-by-frame processing of the video stream can be done in real-time for accurate interaction and gesture detection.

Figure 4:
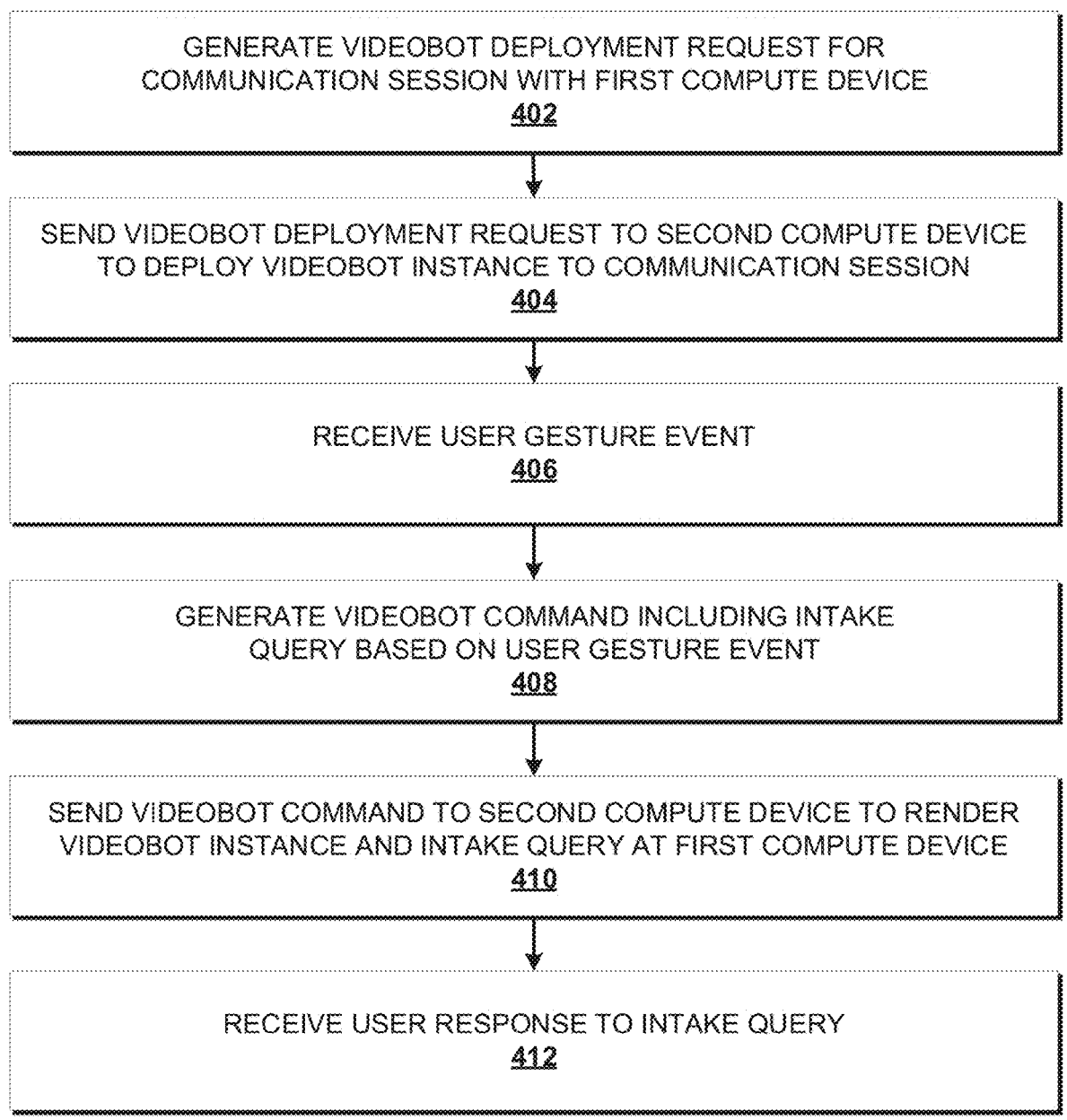
FIG. 4 is a flowchart depicting an example operation of an aspect of a videobot management system, in accordance with an embodiment.

FIG. 4 is a flowchart depicting an example operation of an aspect of a videobot management system 100, in accordance with an embodiment. In some implementations, for example, the example operation may be performed via a device such as patient intake device 120.

At 402, patient intake device 120 generates a videobot deployment request with respect to a communication session with a user at a first compute device to provide a real-time, video-based user-interface between the user and the first compute device via a videobot instance. At 404, patient intake device 120 sends, to a second compute device, the videobot deployment request to cause the first compute device to render the videobot instance during the communication session based on a multimedia stream associated with the videobot instance. In some implementations, the first compute device may include, for example, videobot management platform 130.

At 406, patient intake device 120 receives, from videobot management platform 130, a signal indicating a user gesture event in connection with an act by the user during the communication session. In some implementations, the signal indicating the user gesture event may correspond to output from a medical device disposed within a camera view of user device 110 during the communication session.

At 408, patient intake device 120 generates a videobot command including a patient intake query based on the user gesture event. For example, in some implementations, the patient intake query may be generated to automate collection of information associated with the user (e.g. patient, subject), such as medically relevant information associated with the user, which may be, for example, used to diagnose the user's symptoms or passed along to a medical professional for further analysis. In some implementations, a videobot command may be defined and generated on the basis of parameters relating to verbal and nonverbal communications by a videobot instance, such as in terms of what to say, how to present (visually or in appearance), sentiment, background environment, and/or the like. The command to play audio/video files can be a static file path or a URL pointing to a location on the public internet. The videobot downloads and caches the video file, which can then be incorporated into the multimedia stream associated with the video. This is useful to show the user certain pre-generated content. The command to show a static image file can be static file path or an URL pointing to a location on the public internet. The videobot downloads and caches the image file, which can then be incorporated into the multimedia stream associated with the video with continuous frames with the same image. This is useful to show the user certain pre-generated content or menus.

In some implementations, for example, the videobot command may be executed to display a human face. In such implementations, the videobot command may be generated to include instructions for generating random head or facial movements or expressions, matching speech (audio) to mouth movement, and merging the head, facial, and/or mouth movements. Execution of the command by user device 110 causes user device 110 to render a corresponding video frame, accordingly.

In some implementations, a videobot command may include instructions for rendering a viseme or generic facial image with respect to the videobot instance in association with a particular sentiment to be expressed. For example, the videobot command may be executed to cause the videobot to be rendered with a particular human face with certain text and sentiment for conveying a particular message. In some cases, a text-to-speech engine is used to generate the associated audio file.

At 410, patient intake device 120 sends, to the second compute device, the videobot command to cause the first compute device to render the videobot instance in conjunction with the patient intake query. In some implementations, the patient intake query includes a question about a symptom(s).

At 412, patient intake device 120 receives, from the second compute device, a response by the user to the patient intake query, the response including an indication of patient intake information associated with the user. In some implementations, the patient intake information associated with the user includes a medical history of the user.

As another example, in some implementations, patient intake device 120 may be configured to perform a symptom checker workflow. In some implementations, the symptom checker workflow may include a fully automated video-based medical consultation where an external application (e.g., patient intake application 121 hosted on patient intake device 120) will ask a series of questions about symptoms to the user via user device 110, then use its existing symptom checker workflow to ask further questions and produce possible conditions. For example, the symptom checker workflow may include a verbal communication such as a question (e.g., "what's wrong?") asked by patient intake device 120 via a videobot instance, to which the user may respond with a verbal and/or nonverbal communication, such as speech or a hand gesture. Patient intake device 120 may receive the answer via the videobot instance and ask a follow-up question, accordingly. Such question and answer rounds may continue until patient intake device 120 determines and provides information regarding a potential diagnosis (e.g., by showing a video regarding the associated condition). These workflows can be initiated from a patient interacting directly with the system (e.g., via user device 110) or an acute care professional, such as a nurse or paramedic to help intake a patient, such as by automating a patient or subject intake task.

As another example, in some implementations, patient intake device 120 may be configured to perform an acute care intake task or workflow. For example, medical professionals may initiate interaction with a videobot instance (e.g., via user device 110, patient intake device 120) to automate patient intake tasks such as determining and providing a patient's demographic information, chief complaint, and medical device readings data. In some implementations, for example, the medical device readings data or patient intake information may include medical data associated with a computer-readable medicine label. For example, OCR and QR code technologies are used to detect output (e.g., text) from medical devices and sent to EA. The video stream is able to analyze the frames in the video to automatically recognize the medical device and read the output automatically, simply by showing results to the camera.

As another example, in some implementations, such as when patients show up in urgent care facilities such as emergency rooms or urgent care clinics, patient intake device 120 may include, for example, a kiosk that patients can interact with (e.g., in a manner similar to interaction with user device 110). Patients can then start video calls with the videobots, where they can then perform intake processes for urgent care. The automated videobot can either provide very basic initial assessment of the patient's condition based on the chief complaint, and/or notify the healthcare staff accordingly, until a nurse is available to interact with the patient.

As another example, in some implementations, patient intake device 120 may determine when to remind a patient about their healthcare, based on the health system's electric medical records, such as to call the patient to show or display a short video of the reminder. In some implementations, a reminder may include, for example, a notice associated with blood pressure readings, a notice relating to an upcoming schedule appointment, a notice providing health-related feedback, a notice to take medication intake such as by displaying an image of the medication's container or label.

As another example, in some implementations, patient intake device 120 may be configured to provide customer (e.g., patient) support or automation of tasks relating to various technical, billing, healthcare, or facility information, or any other type of support, in accordance with embodiments of the present disclosure. For example, patient intake device 120 may be configured to automate tasks such as those performed by humans at call centers (e.g. to provide customer support, patient support)

Figure 5:
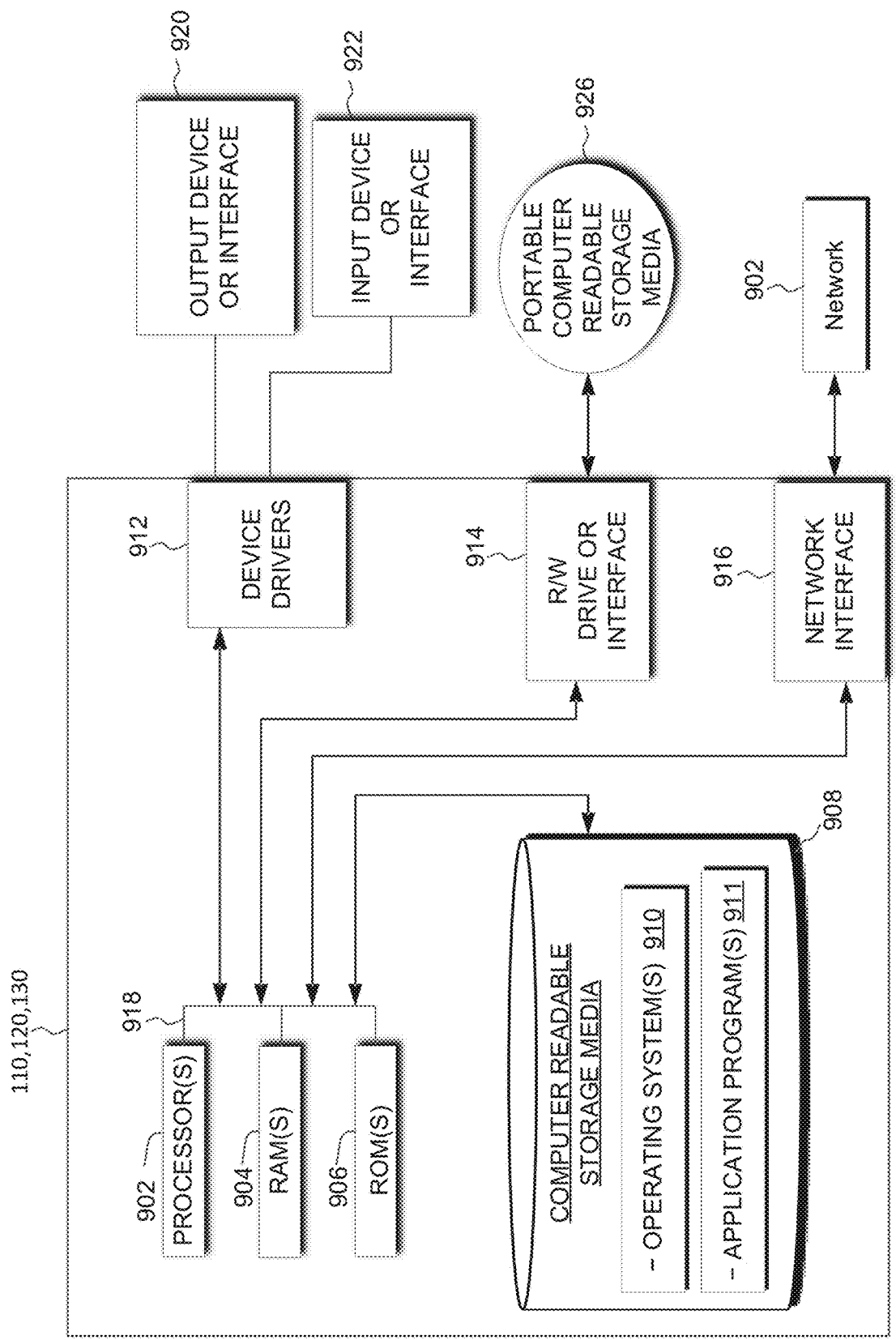
FIG. 5 is a block diagram depicting a user device, a patient intake device, and/or a videobot management platform device, in accordance with an embodiment.

FIG. 5 is a block diagram depicting user device 110, patient intake device 120, and/or videobot management platform device 130, in accordance with an embodiment. As depicted in FIG. 5, user device 110, patient intake device 120, and/or videobot management platform device 130 may include one or more processors 902 (e.g., microprocessors, CPUs, GPUs, etc.), one or more computer-readable RAMs 904, one or more computer-readable ROMs 906, one or more computer readable storage media 908, device drivers 912, read/write drive or interface 914, network adapter or interface 916, all interconnected over a communications fabric 918. The network adapter 916 communicates with a network 930. Communications fabric 918 may be implemented with any architecture designed for passing data and/or control information between processors (such as microprocessors, communications and network processors, etc.), system memory, peripheral devices, and any other hardware components within a system.

As depicted in FIG. 5, one or more operating systems 910 and one or more application programs 911, such as secure videobot management program 131 residing on videobot management platform 130, are stored on one or more of the computer readable storage media 908 for execution by one or more of the processors 902 via one or more of the respective RAMs 904 (which typically include cache memory). In some implementations, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable medium (e.g. a tangible storage device) that can store a computer program and digital information.

User device 110, patient intake device 120, and/or videobot management platform device 130 may also include a read/write (R/W) drive or interface 914 to read from and write to one or more portable computer readable storage media 926. Application programs 911 on viewing device 110 and/or user device 120 may be stored on one or more of the portable computer readable storage media 926, read via the respective R/W drive or interface 914 and loaded into the respective computer readable storage media 908. User device 110, patient intake device 120, and/or videobot management platform device 130 may also include a network adapter or interface 916, such as a Transmission Control Protocol (TCP)/Internet Protocol (IP) adapter card or wireless communication adapter (such as a 4G wireless communication adapter using Orthogonal Frequency Division Multiple Access (OFDMA) technology). For example, application programs 911 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may include copper wires, optical fibers, wireless transmission, routers, firewalls, switches, gateway computers and/or edge servers. User device 110, patient intake device 120, and/or videobot management platform device 130 may also include one or more output devices or interfaces 920 (e.g. a display screen), and one or more input devices or interfaces 922 (e.g. keyboard, keypad, mouse or pointing device, touchpad). For example, device drivers 912 may interface to output devices or interfaces 920 for imaging, to input devices or interfaces 922 for user input or user selection (e.g. via pressure or capacitive sensing), and so on. The device drivers 912, R/W drive or interface 914 and network adapter or interface 916 may include hardware and software (stored on computer readable storage media 908 and/or ROM 906).

Videobot management platform device 130 can be a standalone network server or represent functionality integrated into one or more network systems. User device 110, patient intake device 120, and/or videobot management platform device 130 can be a laptop computer, desktop computer, specialized computer server, or any other computer system known in the art. In some implementations, videobot management platform device 130 represents computer systems using clustered computers and components to act as a single pool of seamless resources when accessed through a network, such as a LAN, WAN, or a combination of the two. This implementation may be desired, particularly for data centers and for cloud computing applications. In general, user device 110, patient intake device 120, and/or videobot management platform device 130 can be any programmable electronic device or can be any combination of such devices, in accordance with embodiments of the present disclosure.

The programs described herein are identified based upon the application for which they are implemented in a specific embodiment or implementation of the present disclosure. That said, any particular program nomenclature herein is used merely for convenience, and thus the embodiments and implementations of the present disclosure should not be limited to use solely in any specific application identified and/or implied by such nomenclature.

Embodiments of the present disclosure may be or use one or more of a device, system, method, and/or computer readable medium at any possible technical detail level of integration. The computer readable medium may include a computer readable storage medium (or media) having computer readable program instructions thereon for causing a processor to carry out one or more aspects of the present disclosure.

The computer readable (storage) medium can be a tangible device that can retain and store instructions for use by an instruction execution device. The computer readable medium may be, but is not limited to, for example, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, in accordance with embodiments of the present disclosure.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some implementations, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform various aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine or system, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks, in accordance with embodiments of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams as shown in the Drawings illustrate the architecture, functionality, and operation of possible implementations of systems, methods, and computer readable media according to various embodiments of the present disclosure. In this regard, each block in the flowchart or block diagrams may represent a module, segment, or portion of instructions, which includes one or more executable instructions for implementing the specified logical function(s). In some implementations, the functions noted in the blocks may occur out of the order noted in the Drawings. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
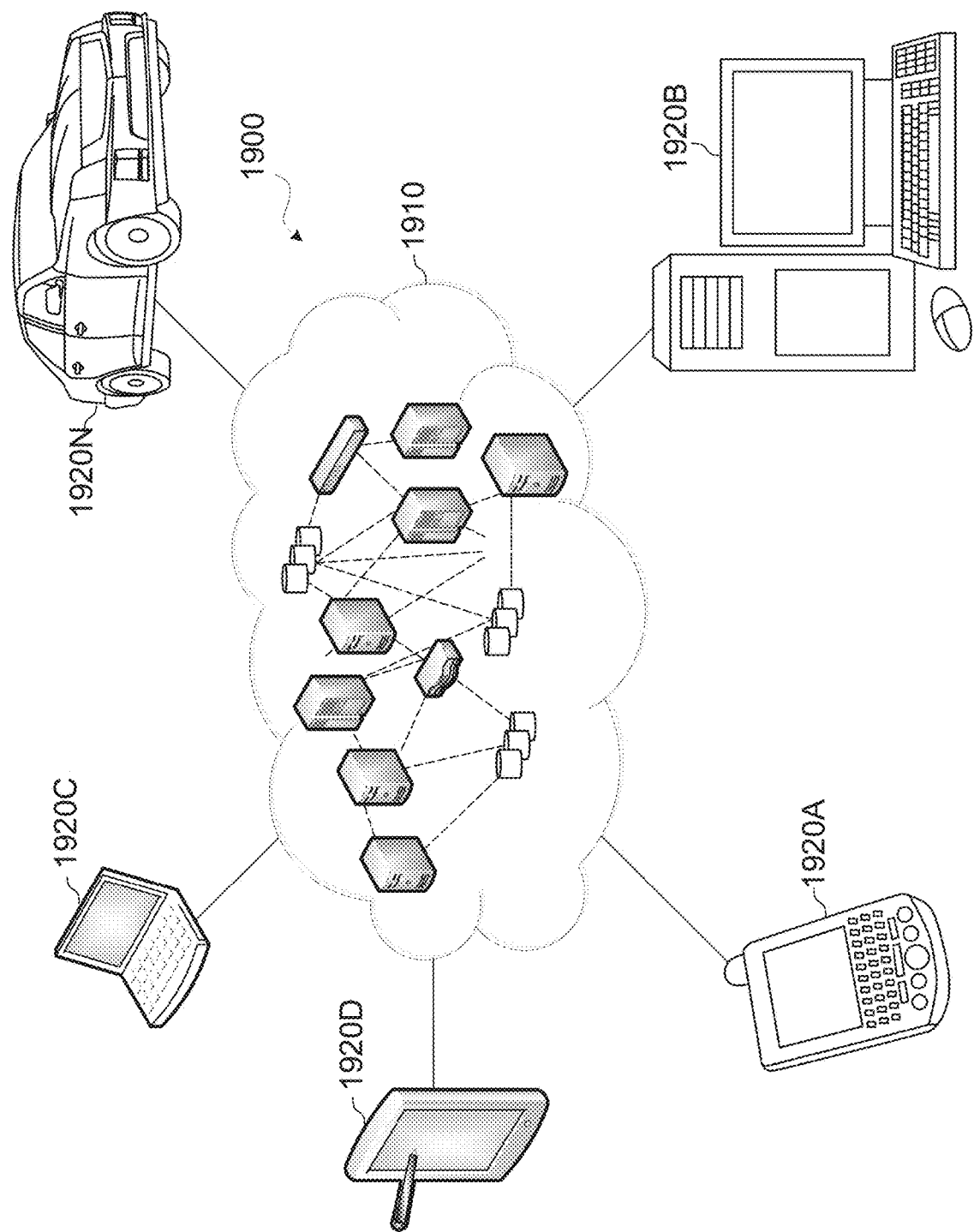
FIG. 6 depicts a cloud computing environment of a videobot management platform, in accordance with an embodiment.

Referring now to FIG. 6, illustrative cloud computing environment 1900 is depicted. As shown, cloud computing environment 1900 includes one or more cloud computing nodes (not depicted) with which local computing devices used by cloud consumers, such as, for example, personal digital assistant (PDA) or cellular telephone 1920A, desktop computer 1920B, laptop computer 1920C, and/or automobile computer system 1920N may communicate. The one or more cloud computing nodes may communicate with one another. They may be grouped (not shown) physically or virtually, in one or more networks, such as Private, Community, Public, or Hybrid clouds as described hereinabove, or a combination thereof. This allows cloud computing environment 1900 may be implemented to offer infrastructure, platforms, and/or software as services for which a cloud consumer does not need to maintain resources on a local computing device. The types of computing devices 1920A-N, as shown in FIG. 6, are intended to be illustrative only and that the one or more computing nodes and cloud computing environment 1900 can communicate with any type of computerized device over any type of network and/or network addressable connection (e.g., using a web browser).

Figure 7:
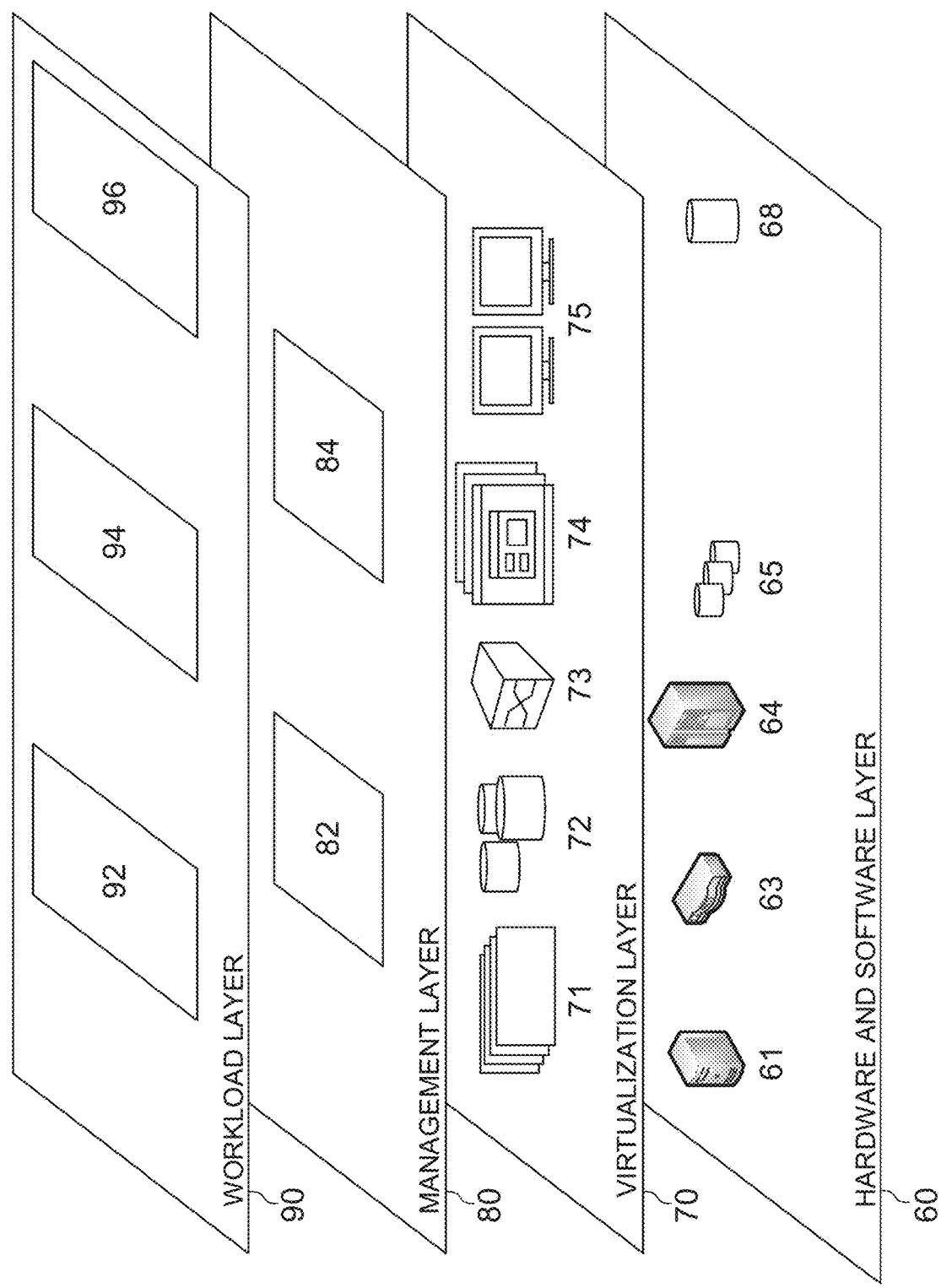
FIG. 7 depicts abstraction model layers of a videobot management platform, in accordance with an embodiment.

Referring now to FIG. 7, a set of functional abstraction layers provided by cloud computing environment 1900 is shown. The components, layers, and functions are intended to be illustrative only, and embodiments of the present disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some implementations, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

As an example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. For example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which a cloud computing environment (e.g. cloud computing environment 1900) may be utilized. Examples of workloads and functions which may be provided from this layer include: mapping and navigation 91; software development and lifecycle management 92; virtual classroom education delivery 93; data analytics processing 94; transaction processing 95; and videobot management 96. Videobot management 96 may include functionality enabling the cloud computing environment to be used to perform videobot management, in accordance with embodiments of the present disclosure.

Detailed embodiments of the present disclosure are disclosed herein for purposes of describing and illustrating claimed structures and methods that may be embodied in various forms, and are not intended to be exhaustive in any way, or limited to the disclosed embodiments. Many modifications and variations will be apparent without departing from the scope of the disclosed embodiments. The terminology used herein was chosen to best explain the principles of the one or more embodiments, practical applications, or technical improvements over current technologies, or to enable understanding of the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present disclosure herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

While some implementations have been described and illustrated herein, a variety of other means and/or structures for performing the function and/or obtaining the results and/or one or more of the advantages is possible. More generally, parameters, dimensions, materials, and configurations described herein are meant to be exemplary and that the actual parameters, dimensions, materials, and/or configurations will depend upon the specific application or applications for which the inventive teachings is/are used. It is, therefore, to be understood that the foregoing embodiments are presented by way of example only and that, within the scope of the appended claims and equivalents thereto; and that embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

Also, various concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A non-transitory processor-readable medium storing code representing instructions to cause a processor to:
receive, from a first compute device, a videobot deployment request with respect to a communication session with a user at a second compute device;
provision a videobot instance to provide a real-time, video-based user-interface between the user and the videobot instance at the second compute device in response to the videobot deployment request, the videobot instance configured to automate real-time interaction with the user in the communication session via the real-time, video-based user-interface;
send, to the second compute device, data including a message and an indicator of a sentiment to convey the message to cause the second compute device during a time period of the communication session to render the videobot instance including (a) generating a video of a facial expression having the sentiment and generating an audio of the message based on the data, and (b) displaying the video of the facial expression and playing back the audio of the message;
receive, from the second compute device during the time period, a live multimedia stream associated with the user and received during the time period;
rank a plurality of gesture detection algorithms for the videobot instance, and based on past usage of each gesture detection algorithm from the plurality of gesture detection algorithms;
execute at least one gesture detection algorithm from the plurality of gesture detection algorithms to detect the at least one user gesture event, the at least one gesture detection algorithm having a rank above a predetermined threshold;

execute the at least one gesture detection algorithm to detect, from a plurality of frames of the live multimedia stream, at a rate no greater than a frame rate at which the video bot instance is rendered at the second compute device, at least one user gesture event in connection with an act by the user during the time period, the at least one user gesture event corresponding to an indication of a set of patient intake information associated with the user; and in response to detecting the at least one user gesture event, send, to the first compute device, a signal indicating the at least one user gesture event.

2. The non-transitory processor-readable medium of claim 1, wherein the real-time, video-based user-interface is configured to collect medical data associated with the user based on the live multimedia stream.

3. The non-transitory processor-readable medium of claim 1, wherein the time period is a first time period, the at least one user gesture event corresponding to an indication of a first set of patient intake information associated with the user, the medium further comprising code representing instructions to cause the processor to:

receive, from the first compute device, a signal indicating a videobot command in response to sending the signal indicating the at least one user gesture event;

execute the videobot command to cause the second compute device to render the videobot instance in conjunction with a patient intake query during a second time period of the communication session after the first time period;

receive, from the second compute device during the second time period, a live multimedia stream during the second time period;

detect a response to the patient intake query during the second time period based on at least one video frame of the live multimedia stream during the second time period, the response including an indication of a second set of patient intake information associated with the user; and in response to detecting the response, send, to the first compute device, a signal indicating the response.

4. The non-transitory processor-readable medium of claim 3, wherein the at least one user gesture event is detected by execution of a computer vision algorithm, a speech recognition algorithm, the at least one gesture detection algorithm, an optical character recognition algorithm, and a barcode processing algorithm.

5. The non-transitory processor-readable medium of claim 4, wherein the neural network includes a recurrent neural network.

6. The non-transitory processor-readable medium of claim 3, wherein the second set of patient intake information includes medical data associated with a computer-readable medicine label.

7. The non-transitory processor-readable medium of claim 3, wherein the second set of patient intake information includes medical data associated with an output from a medical device.

8. A non-transitory processor-readable medium storing code representing instructions to cause a processor to:

generate a videobot deployment request with respect to a communication session;

send, to a first compute device, the videobot deployment request;

receive, at a first compute device from a second compute device and in response to sending the videobot deployment request, data including a message and an indicator of a sentiment to convey the message;

render a videobot instance based on data during a first time period of the communication session to provide a real-time, video-based user-interface between a user and the videobot instance, rendering the videobot instance including (a) generating a video of a facial expression having the sentiment and generating an audio of the message based on the data, and (b) displaying the video of the facial expression and playing back the audio of the message;

send, to the second compute device during the first time period, a live multimedia stream associated with the user such that a plurality of frames of the live multimedia stream are monitored to detect, at a rate no greater than a frame rate of the rendering of the video bot instance, at least one user gesture event during the first time period, the at least one gesture event generated at the second compute device via:

(A) ranking a plurality of gesture detection algorithms for the videobot instance, and based on past usage of each gesture detection algorithm from the plurality of gesture detection algorithms, and (B) executing at least one gesture detection algorithm from the plurality of gesture detection algorithms to detect the at least one user gesture event, the at least one gesture detection algorithm having a rank above a predetermined threshold;

determine a first frame process window ("FPW") value based on a frame rate of rendering of the videobot instance during the first time period;

determine a first frame processing time ("FPT") value associated with each of one or more processes based on an amount of time taken by each of the one or more processes to detect the at least one user gesture event during the first time period, respectively;

determine a first, actual frame process window ("AFPW") value based on a sum of the first FPT value associated with each of the one or more processes, collectively; and in response to determining that the first FPW value exceeds the first AFPW, perform a remedial action to define a frame rate of rendering the videobot instance during a second time period of the communication session after the first time period, a second FPW value of the videobot instance during the second time period being based on the frame rate of the rendering the videobot instance during the second time period and being less than the first FPW value.

9. The non-transitory processor-readable medium of claim 8, wherein the first FPW value and the second FPW value each is determined according to one or more commands received from the second compute device.

10. The non-transitory processor-readable medium of claim 8, wherein the remedial action is performed according to one or more commands received from the second compute device.

11. The non-transitory processor-readable medium of claim 8, wherein the remedial action is performed to reduce a latency between the rendering of the videobot instance and the received multimedia stream during the second time period.

12. The non-transitory processor-readable medium of claim 8, wherein the remedial action is performed to skip at least one frame during the rendering of the videobot instance during the second time period.

13. The non-transitory processor-readable medium of claim 8, wherein the remedial action is performed to reduce a video frame pixel density of at least one frame during the rendering of the videobot instance during the second time period.

14. The non-transitory processor-readable medium of claim 8, wherein the remedial action is performed to skip execution of at least one image processing algorithm during the second time period based on a use value of the image processing algorithm relative to use values of at least one other image processing algorithm.

15. The non-transitory processor-readable medium of claim 8, wherein the remedial action is performed to execute at least two image processing algorithms in parallel during the second time period.

16. A non-transitory processor-readable medium storing code representing instructions to cause a processor to:
generate a videobot deployment request with respect to a communication session with a user at a first compute device to provide a real-time, video-based user-interface between the user and the first compute device via a videobot instance, the videobot instance configured to automate real-time interaction with the user in the communication session via the real-time, video-based user-interface;
send, to a second compute device, the videobot deployment request to cause the first compute device to render the videobot instance during the communication session based on a data including a message and an indicator of a sentiment to convey the message, rendering the videobot instance including (a) generating a video of a facial expression having the sentiment and generating an audio of the message based on the data, and (b) displaying the video of the facial expression and playing back the audio of the message;
receive, from the second compute device, a signal indicating at least one user gesture event in connection with an act by the user during the communication session, the signal generated at the second compute device via
(1) monitoring of a live multimedia stream associated with the user and received at the second compute device during the time period, the live multimedia stream including a plurality of frames,
(2) ranking a plurality of gesture detection algorithms for the videobot instance, and based on past usage of each gesture detection algorithm from the plurality of gesture detection algorithms, and
(3) executing at least one gesture detection algorithm from the plurality of gesture detection algorithms to detect the at least one user gesture event based on the individual frame from the plurality of frames of the live multimedia stream at a rate no greater than a frame rate at which the video bot instance is rendered at the first compute device;
generate a videobot command including a patient intake query based on the at least one user gesture event;
send, to the second compute device, the videobot command to cause the first compute device to render the videobot instance in conjunction with the patient intake query; and
receive, from the second compute device, a response by the user to the patient intake query, the response including an indication of patient intake information associated with the user,
the at least one user gesture event including a symptomatic act by the user during the communication session, the symptomatic act associated with the indication of patient intake information associated with the user, and
the detecting of the at least one user gesture event including determining a first frame processing time ("FPT") of each of one or more processes executed in detecting the at least one user gesture event, based on an amount of time taken by each of the one or more processes to detect the at least one user gesture event during the first time period, respectively.

17. The non-transitory processor-readable medium of claim 16, wherein the patient intake query includes a symptomatic question.

18. The non-transitory processor-readable medium of claim 16, wherein the videobot command is a first videobot command, the medium further comprising code representing instructions to cause the processor to:
determine a chief complaint of the user;
determine a medical condition likely to be associated with the user;
determine a likelihood of actual association between the medical condition and the user;
in response to determining that the likelihood exceeds a predetermined threshold, determine a prognosis of the medical condition with respect to the user based on the patient intake information, the at least one user gesture event, the medical condition, and the chief complaint;
generate a second videobot command including a suggested patient treatment plan based on the prognosis; and
send, to the second compute device, the second videobot command to cause the first compute device to render the videobot instance in conjunction with the suggested patient treatment plan.

19. The non-transitory processor-readable medium of claim 18, wherein the medical condition is determined based on medical data associated with a computer-readable medicine label of a medicine container disposed within a camera view of the first user compute device.

20. The non-transitory processor-readable medium of claim 16, wherein the patient intake information includes a medical history of the user.

21. The non-transitory processor-readable medium of claim 18, wherein the medical condition is determined based on an output from a medical device disposed within a camera view of at the first user compute device.

22. The non-transitory processor-readable medium of claim 1, wherein
the at least one user gesture event including the symptomatic act by the user is a nonverbal, unconsciously-expressed symptomatic act by the user, and
the at least one user gesture event is detected in connection with an act of at least one of verbal communication or nonverbal communication by the user during the time period.

23. The non-transitory processor-readable medium of claim 1, wherein the plurality of gesture detection algorithms includes an age detection algorithm, a gender detection algorithm, an identity recognition algorithm, an attention detection algorithm, a mouth detection algorithm, and a hand gesture recognition algorithm.

* * * * *